(12) United States Patent
Donomae

(10) Patent No.: US 7,852,513 B2
(45) Date of Patent: Dec. 14, 2010

(54) COLOR CHART FOR ADJUSTING COLORS AND COLOR ADJUSTING METHOD

(75) Inventor: Yoshifumi Donomae, Kawasaki (JP)

(73) Assignee: FUJIFILM Corporation (JP)

( * ) Notice: Subject to any disclaimer, the term of this patent is extended or adjusted under 35 U.S.C. 154(b) by 780 days.

(21) Appl. No.: 11/717,017

(22) Filed: Mar. 13, 2007

(65) Prior Publication Data

US 2007/0211274 A1 Sep. 13, 2007

(30) Foreign Application Priority Data

Mar. 13, 2006 (JP) ............................. 2006-066946

(51) Int. Cl.
*H04N 1/40* (2006.01)
(52) U.S. Cl. ....................................... 358/2.1; 358/504
(58) Field of Classification Search .................. 358/1.9, 358/2.1, 500, 504, 527, 516–519
See application file for complete search history.

(56) References Cited

U.S. PATENT DOCUMENTS 4,527,895 A * 7/1985 Rubin .......................... 356/30
6,075,888 A * 6/2000 Schwartz ..................... 382/167

FOREIGN PATENT DOCUMENTS

JP 60105928 A * 6/1985
JP 2005-043105 A 2/2005

* cited by examiner

*Primary Examiner*—Thomas D Lee
*Assistant Examiner*—Stephen M Brinich
(74) *Attorney, Agent, or Firm*—Sughrue Mion, PLLC (57) ABSTRACT

A color chart that enables exact color adjustments without being influenced by distortion or peripheral light loss is provided. The color chart has a plurality of colored regions each being of a different color, separated by line segments that radiate outward from a predetermined point. A plurality of achromatic colored regions are provided among the plurality of colored regions at predetermined intervals.

8 Claims, 9 Drawing Sheets

81 COLORS

|     | R | G  | B   |
|-----|---|----|-----|
| $C_1$  | 0 | 0  | 0   |
| $C_2$  | 0 | 0  | 32  |
| $C_3$  | 0 | 0  | 64  |
| $C_9$  | 0 | 0  | 256 |
| $C_{10}$ | 0 | 32 | 0   |
| $C_{11}$ | 0 | 32 | 32  |
| $C_{18}$ | 0 | 32 | 256 |
| $C_{19}$ | 0 | 64 | 0   |
| $C_{20}$ | 0 | 64 | 32  |

} 81 COLORS

FIG.12A ACTUAL SPACE

FIG.12B IMAGED SPACE

FIG.12C

CORRELATION BETWEEN DISTANCES

COLOR CHART FOR ADJUSTING COLORS AND COLOR ADJUSTING METHOD

BACKGROUND OF THE INVENTION

1. Field of the Invention

The present invention relates to a color chart for color adjustment, and to a color adjusting method.

2. Description of the Related Art

Endoscopes are in wide use in the medical field. Point light sources of illuminating sections provided in the vicinities of imaging sections of color endoscopes illuminate the interiors of body cavities during imaging using endoscopes. Obtained images are reproduced by color monitors, color printers and the like.

Observation and examination of the interiors of body cavities are based on images obtained by endoscopes. Therefore, it is desirable for the images to be output in colors as close to the actual colors as possible. However, different endoscopes have different color imaging ranges and color reproduction ranges. Accordingly, different color properties are exhibited by each endoscope.

In addition, point light sources provided in the vicinities of imaging sections of color endoscopes are employed to illuminate the interiors of body cavities during imaging. However, it is not possible to uniformly illuminate the entirety of the interior of a body cavity with a point light source. Therefore, a phenomenon called "peripheral light loss", in which light is insufficient toward the outer periphery of an imaging lens and the periphery of images become dark, occurs. Further, wide angle lenses having short focal distances are utilized in the imaging sections of color endoscopes, in order to image the narrow interiors of body cavities. Therefore, distortion, in which straight lines are imaged as curves, occurs as well.

For example, in the case that a latticed color chart is imaged, the shapes of the colored regions that constitute the color chart are changed by distortion, and may become "barrel-shaped", in which the center portion is swollen, or "bobbin-shaped", in which the center portion is constricted. In addition, the image of the color chart is output such that the peripheral portion is darker than the central portion thereof, due to the aforementioned peripheral light loss. There is a possibility that the distortion and/or the peripheral light loss may cause erroneous judgments during color adjustment.

Japanese Unexamined Patent Publication No. 2005-043105 proposes a method for color adjustment for output of images obtained by endoscopes through color printers and color monitors. In this method, a color chart comprising radially spreading fan shaped colored regions is employed, to enable color adjustment which is not influenced by peripheral light loss or distortion.

However, the influence caused by peripheral light loss and distortion cannot be completely eliminated, even if the aforementioned color chart comprising fan shaped colored regions is employed. For this reason, the position within the color chart and changes in brightness cannot be accurately judged based on obtained images, and exact color matching cannot be performed.

SUMMARY OF THE INVENTION

The present invention has been developed in view of the foregoing circumstances. It is an object of the present invention to provide a color chart that enables exact color adjustments without being influenced by distortion or peripheral light loss, and a color adjusting method.

A color chart of the present invention comprises:

a plurality of colored regions each being of a different color and separated by line segments that radiate outward from a predetermined point; and a plurality of achromatic colored regions which are provided among the plurality of colored regions at predetermined intervals.

The "colored regions" are regions which are respectively colored by a single color.

The "achromatic colored regions" are regions colored by an achromatic color. The achromatic color is a color that bears data regarding only brightness of three primary colors, and refers to colors without hue, such as white, gray, and black.

It is preferable for the achromatic colored regions to be neutral gray regions.

The color chart of the present invention may be employed to adjust colors within images obtained by endoscopes.

A method for adjusting colors of the present invention is a method for adjusting colors within an image obtained by an endoscope, comprising the steps of:

obtaining a color chart image of the aforementioned color chart with the endoscope, from directly in front of the predetermined point of the color chart;

detecting the achromatic regions of the color chart from within the color chart image;

estimating the brightness of the colored regions within the color chart image, based on the brightness of the achromatic regions; and adjusting the colors that appear within the image obtained by the endoscope, based on the pixel values at positions within the color chart image, at which the estimated brightness of the colored regions is constant.

It is desirable for the adjustment of colors to be performed by employing a look up table, in which pixel values at the positions within the color chart image at which the estimated brightness of the colored regions is constant are correlated to pixels values of the corresponding colored regions within the color chart.

The color chart of the present invention comprises the colored regions, which are separated by radially spreading line segments. Therefore, when imaging is performed with an imaging device that employs a wide angle lens, an image, on which influence due to distortion is minimal, can be obtained. In addition, by providing the achromatic colored regions at predetermined intervals, the influence due to peripheral light loss can be accurately detected. Accordingly, colors can be accurately adjusted.

If the achromatic colored regions are colored neutral gray, the influence of peripheral light loss is more easily observed than if the achromatic colored regions are white or black.

The color chart of the present invention is particularly suited for adjusting colors of images obtained by endoscopes that illuminate subjects with light sources in the vicinities of wide angle lenses.

BRIEF DESCRIPTION OF THE DRAWINGS

FIG. 10 is a diagram for explaining how the central point of a radial color chart image is searched for.

FIGS. 11A and 11B are diagrams for explaining how the first and last regions of a rectangular color chart image are searched for.

FIGS. 13A and 13B are graphs for explaining how neutral gray regions are searched for.

DESCRIPTION OF THE PREFERRED EMBODIMENTS

Hereinafter, an embodiment of the present invention will be described in detail with reference to the attached drawings. First, an endoscope 100 that performs imaging will be described with reference to FIG. 1 and FIG. 2.

Figure 1:
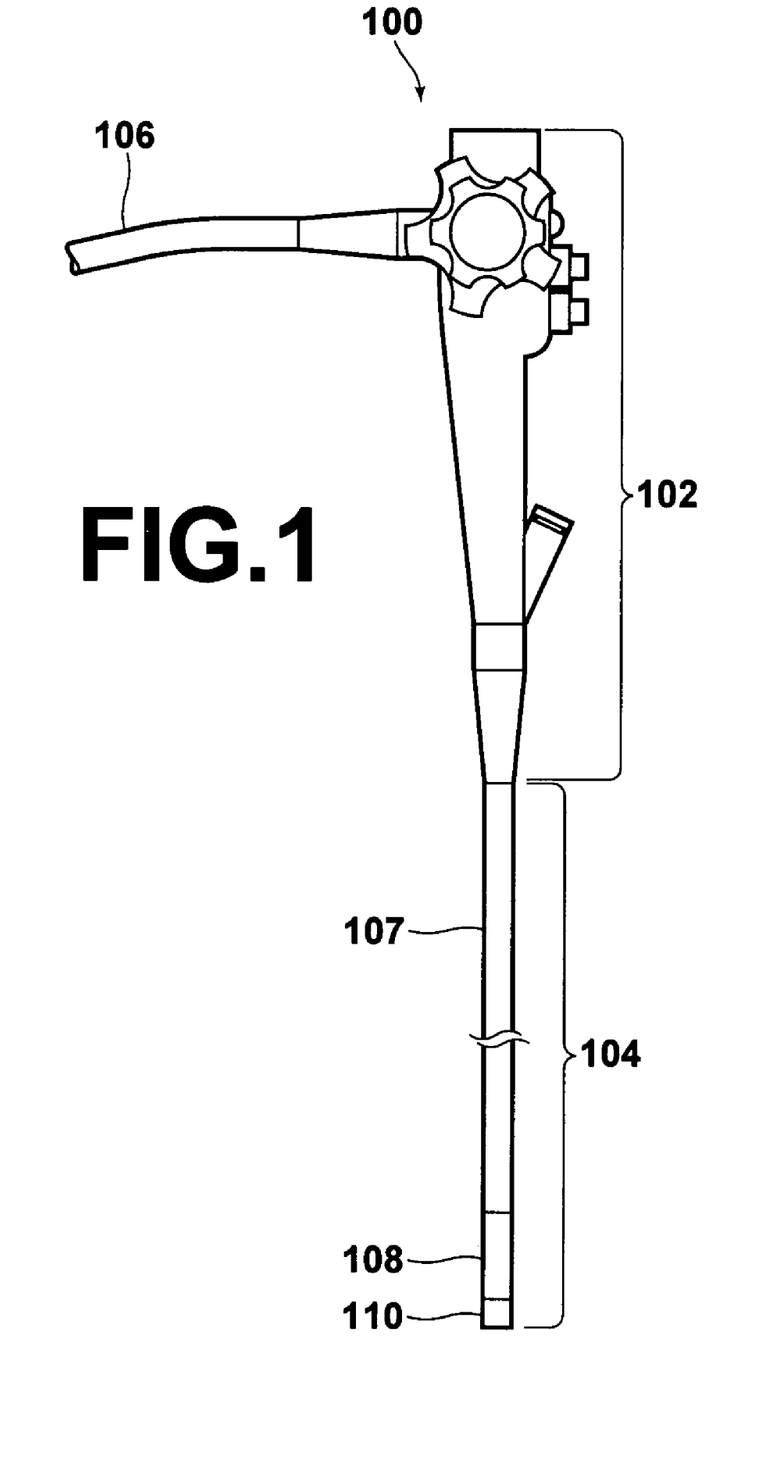
FIG. 1 is a view that illustrates the construction of an endoscope.

As illustrated in FIG. 1, the endoscope 100 comprises: an operating portion 102; an insertion portion 104; and a connector portion (not shown) through which a universal cord 106 is drawn.

The connector portion is connected to a monitor for reproducing images, a light source apparatus, and the like.

The insertion portion 104, which is inserted into body cavities of patients, is continuous with the operating portion 102. The universal cord 106, which is connected to the light source apparatus and the like, is attached to the operating portion 102.

A large portion of the insertion portion 104 is a flexible portion 107, which bends in desired directions along an insertion path. An angling portion 108 is provided at the distal end of the flexible portion 107, and a distal end portion 110 is provided at the distal end of the angling portion 108. The angling portion 108 is provided to enable the distal end portion 110 to face desired directions, and is bendable by manual operations at the operating portion 102.

Figure 2:
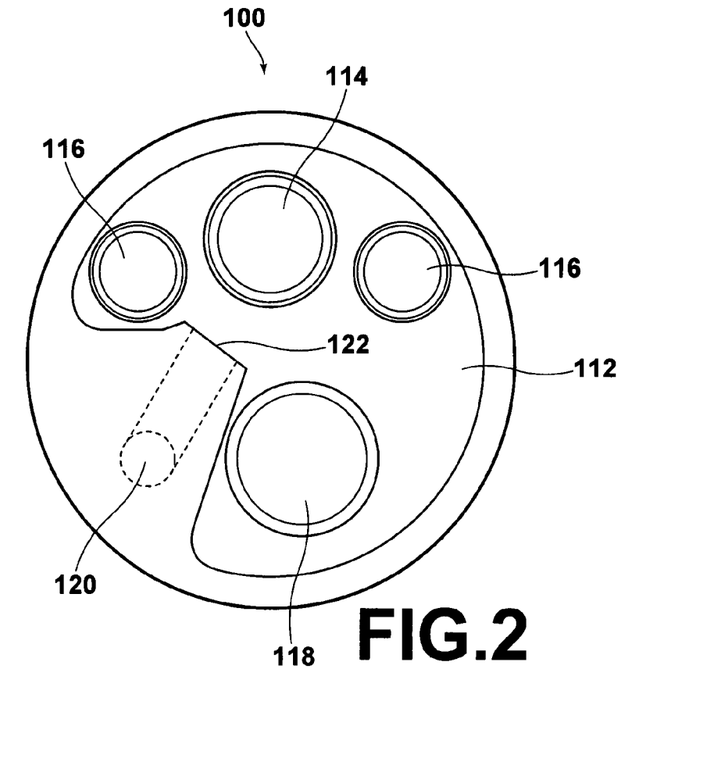
FIG. 2 is a view that illustrates the construction of the distal end of the endoscope

As illustrated in FIG. 2, an imaging window 114, an illuminating window 116, an opening 118, and an opening 120 are provided in the distal end side of a distal end main body 112, which is embedded in the distal end portion 110. The imaging window 114 constitutes a portion of an imaging system for imaging subjects. The illuminating window 116 constitutes a portion of an illuminating system for emitting illuminating light toward subjects. The opening 118 constitutes a portion of a suctioning mechanism for suctioning bodily fluids during procedures, and is also an opening through which implements such as forceps are inserted into the body cavities of patents. The opening 120 is an opening for an air/water supply tubing network that constitutes a portion of an air/water supply mechanism for cleansing the imaging window 114 and the like.

A light emitting end of a light guide (not shown) faces the illuminating window 116, and the interiors of body cavities are illuminated by illuminating light, which propagates from a light source apparatus through the light guide. The light guide is incorporated within the insertion section 104, the operating portion 102, and the universal cord 106.

An objective lens is provided in the imaging window 114, and an imaging device such as a miniature high performance camera (CCD) for imaging subjects through the objective lens is provided in the distal end portion main body 112. Images obtained by the imaging device are transmitted to the monitor (not shown) via a cable that extends through the insertion portion 104, the operating portion 102, and the universal cord 106.

Figure 3:
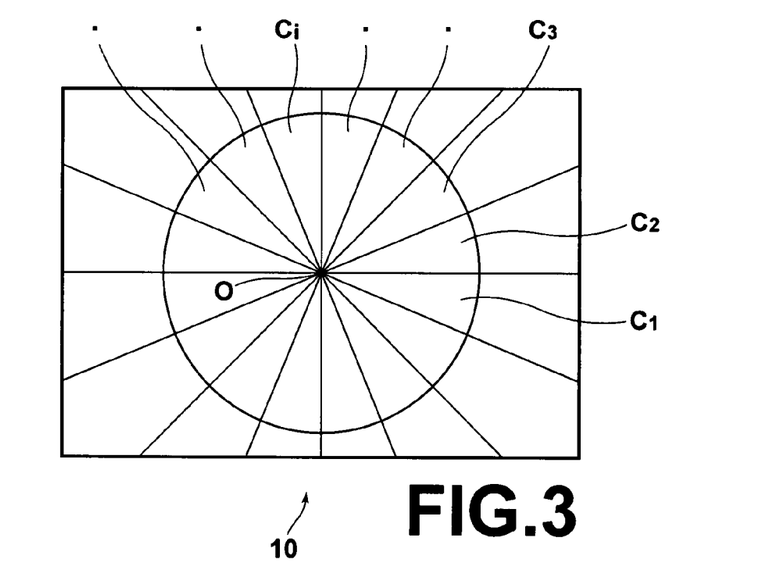
FIG. 3 is a diagram that illustrates a first example of a color chart.
Figure 4:
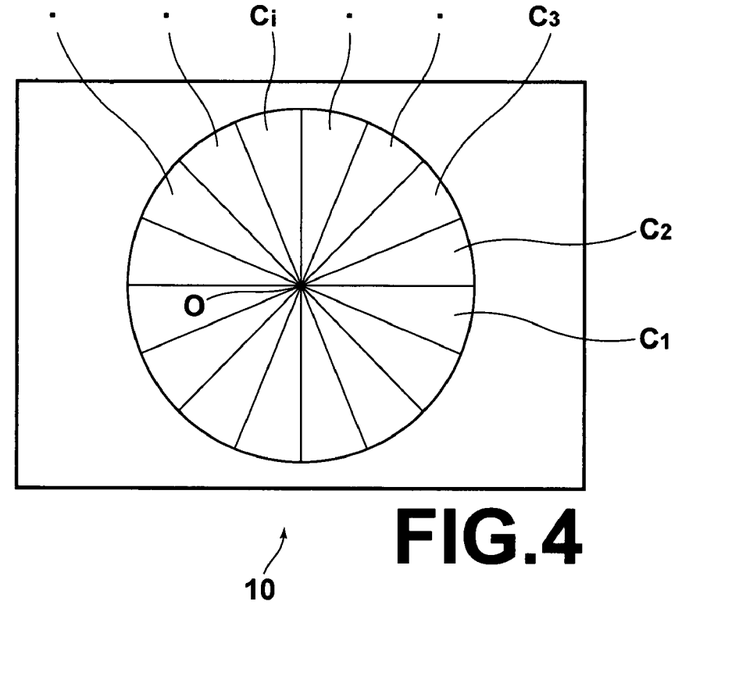
FIG. 4 is a diagram that illustrates a second example of a color chart.
Figure 5:
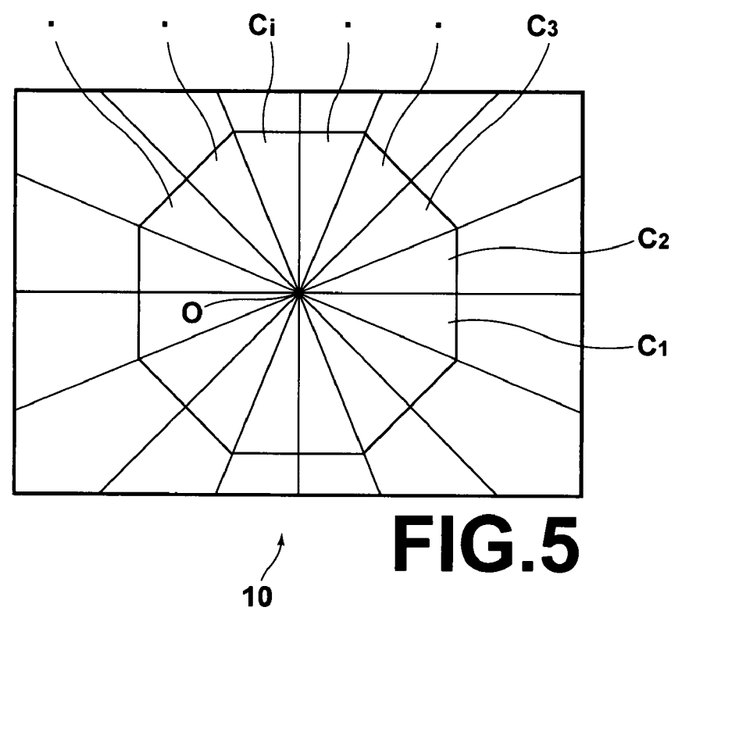
FIG. 5 is a diagram that illustrates a third example of a color chart.

A color chart 10 has a plurality of colored regions $C_1, C_2, C_3, \ldots C_i$, which are separated by line segments that extend radially from a central point O, as illustrated in FIG. 3. Alternatively, the colored regions of the color chart 10 may be wedge shaped regions of a circle, separated by line segments that extend radially from the center thereof, as illustrated in FIG. 4. The colored regions may extend outside the outline of the circle. As a further alternative, the outline of the combined colored regions may form a polygonal shape, as illustrated in FIG. 5. The color chart 10 may be in any form, as long as the colored regions are separated by radially extending lines at the center of an image thereof obtained by the endoscope 100, such that influence is not exerted by peripheral light loss or distortion. The colored regions need not be separated by lines that extend radially from the exact center of the color chart 10, as long as the lines extend radially outward from a point in the vicinity of the center of the color chart 10.

Figure 6A:
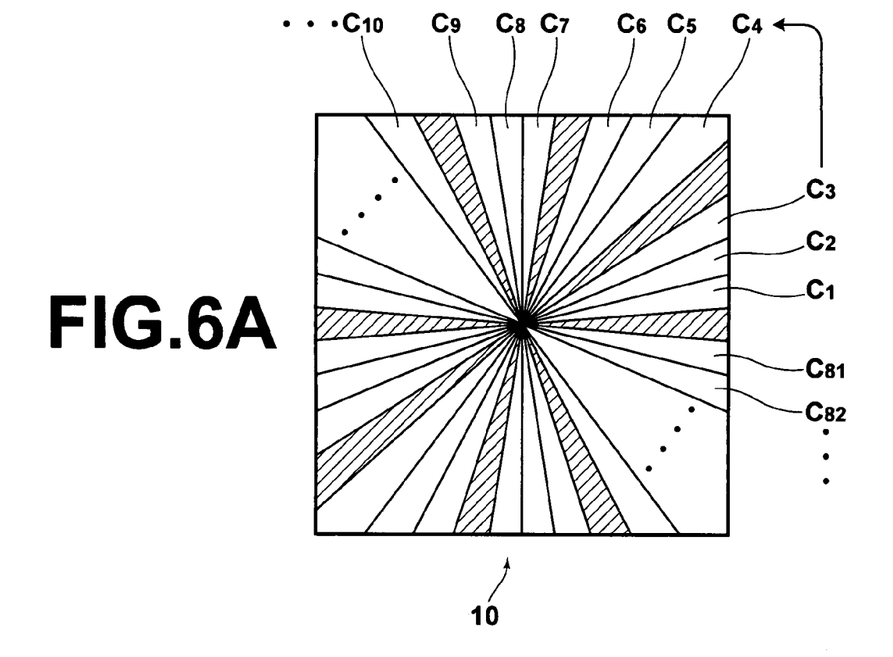
FIG. 6A is a diagram that illustrates a fourth example of a color chart.

As illustrated in FIG. 6A, the color chart 10 of the present embodiment comprises colored regions, which are separated by line segments that extend radially outward at regular angular intervals from a central point O. In addition, achromatic colored regions (indicated by the hatched portions) are provided at predetermined intervals. Hereinafter, a case in which each of R, G, and B values are represented by 8 bit data that takes values from 0 to 255 will be described.

The colored regions are of colors in which the values of R, G, and B are gradually varied, respectively. In the case that the color chart 10 is constituted by colored regions, each of which are of colors in which the R, G, and B values are varied by 32, the number of colored regions will be $9^3=729$. In the case that 729 colored regions are provided at regular angular intervals from the center of the color chart 10 as illustrated in FIG. 6A, each colored region becomes narrow, and discrimination of colors within an obtained image thereof becomes difficult. Therefore, nine color charts 10, each comprising 81 colored regions, are generated.

Figure 6B:
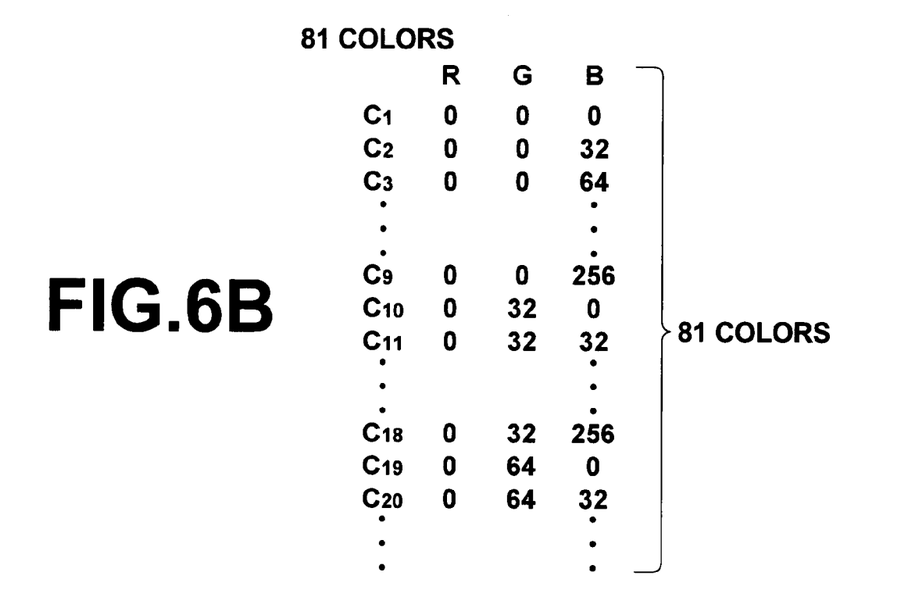
FIG. 6B is a table that illustrates RGB values within the color chart.

As illustrated in the table of FIG. 6B, a first color chart 10 comprises 81 colored regions. The R values of the colors of the colored regions are fixed at 0, and the G and B values are varied in increments of 32 from 0 through 255, respectively. Further, neutral gray regions (the hatched portions in FIG. 6A) are inserted for every three colored regions within the color chart 10. The R value of the colors of the colored regions are fixed at 32 in the second color chart 10, 64 in the third color chart 10, and so on until the ninth color chart 10, in which the R value is 255. The G and B values of the colors of the 81 colored regions within each of the second and subsequent color charts 10 are varied by 32, and neutral gray regions are inserted for every three colored regions within the color charts 10.

Hereinafter, a method by which color adjustment is performed based on a color chart image, obtained by the endoscope 100 obtaining an image of the color chart 10 of FIG. 6, will be described.

First, the color chart 10 is placed such that the imaging window 114 of the endoscope 100 is along a line normal to the central point O of the color chart 10. Then, the color chart 10 is illuminated with light emitted through the illuminating window 116 and an image thereof is obtained by the imaging system. A wide angle lens is employed as the objective lens in the imaging window 114. Therefore, in the case that a latticed color chart is imaged, the shapes of the colored regions that constitute the color chart are changed by distortion, and may become "barrel-shaped", in which the center portion is swollen. If the objective lens is on a line normal to the central point of the color chart 10, the influence of distortion is not observed, and the border of the colored regions appear as straight lines. However, in the case that the objective lens is at a position shifted from the central point of the color chart 10, the borders of the colored regions will appear as straight lines at the center of the image, but will be distorted toward the outside, due to distortion.

The illuminating window 116 is provided close to the imaging window 114, and imaging is performed with the illuminating light being emitted from the vicinity of the objective lens. Therefore, even though the brightness within each of the colored regions is uniform, the obtained color chart image becomes darker toward the outside, due to peripheral light loss.

The steps by which color adjustment is performed by searching for values of colors that appear in the colored regions of the color chart image will be described with reference to the flow chart of FIG. 7.

Figures 7, 8:
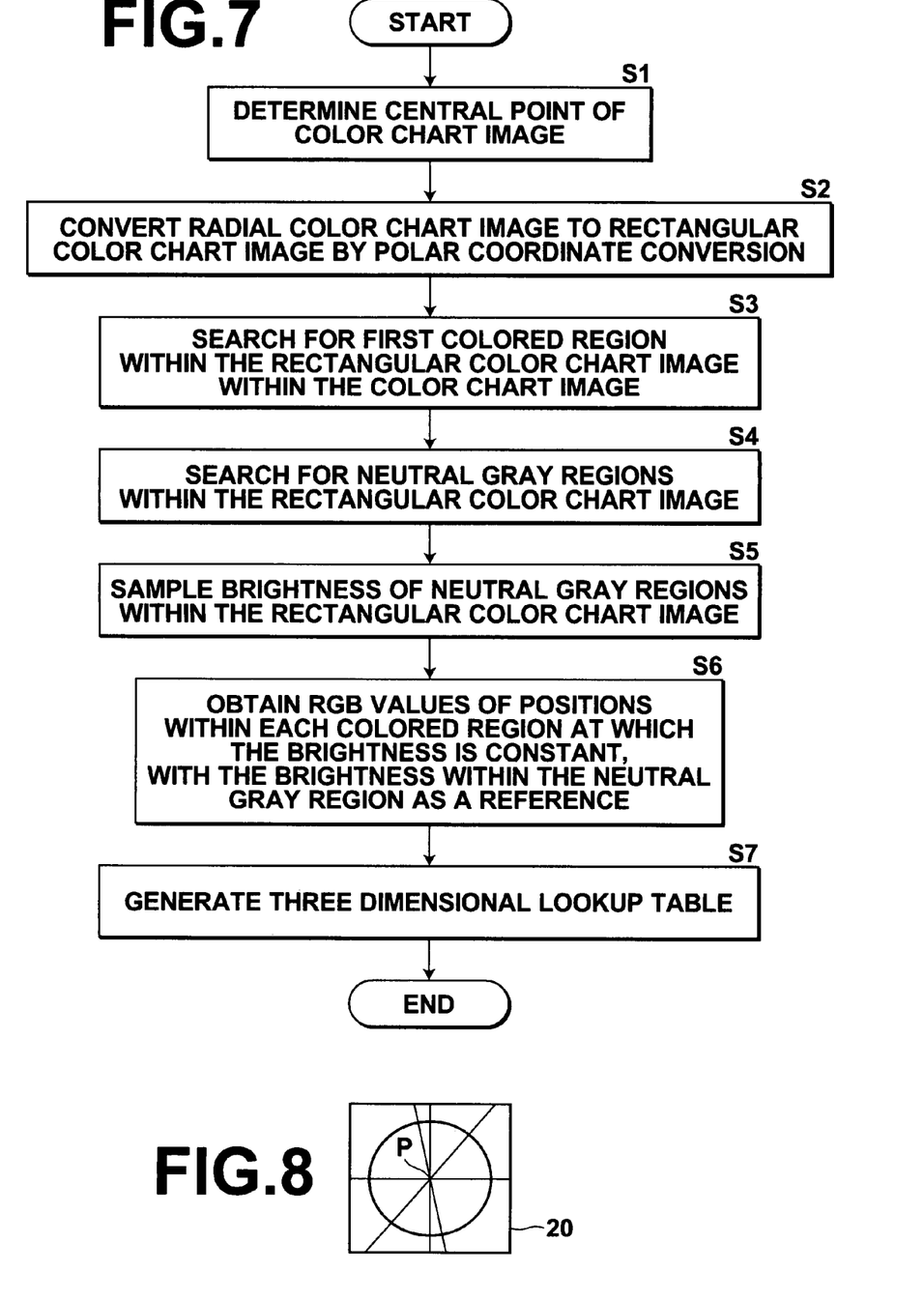
FIG. 7 is a flow chart that illustrates the steps of a color adjusting process.
FIG. 8 is a diagram for explaining the central point of a radial color chart image.

Step 1: the coordinates of a central point P (x, y) of the borders of the colored regions are searched for within the color chart image 20, as illustrated in FIG. 8.

Step 2: the color chart image 20 is converted to a rectangular color chart image 20 by administering polar coordinate conversion with the central point P as a reference.

Step 3: the colored region which is the first colored region within the rectangular color chart image 30 is searched for within the color chart image 20.

Step 4: the neutral gray regions are searched for within the rectangular color chart image 30.

Step 5: the brightness of the neutral gray regions within the rectangular color chart image 30 is sampled.

Step 6: RGB values of the colored regions are obtained at positions within each of the colored regions within the rectangular color chart image 30 at which the brightness is constant, with the brightness of the neutral gray region as a reference.

Step 7: a three dimensional look up table is generated from RGB values of the colored regions within the rectangular color chart image 30 and the RGB values of the corresponding colored regions within the color chart 10.

The aforementioned steps will be described in detail below.

First, the coordinates of a central point P (x, y) of the borders of the colored regions are searched for within the color chart image 20.

Figure 10:
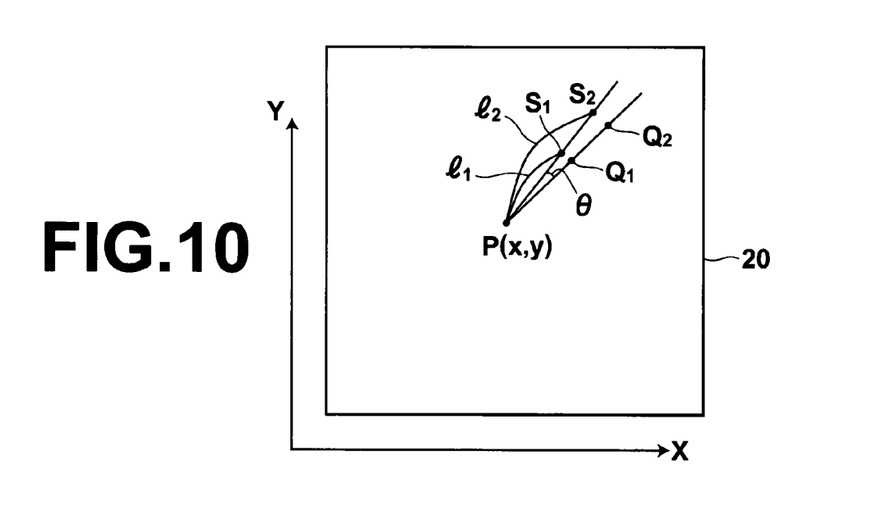

As illustrated in FIG. 10, an arbitrary point P (x, y) in the vicinity of the center of the radial color chart image 20 is set as the central point. The pixel value of a point $S_1$, which is a distance $l_1$ from the point P along a line L that passes through the point P is designated as $a_1$. The pixel value of a point $Q_1$, which is the point $S_1$ rotated θ degrees with the point P as the center of rotation, is designated as $b_1$. Then, the pixel value of a point $S_2$, which is a distance $l_2$ from the point P along the line L is designated as $a_2$. The pixel value of a point $Q_2$, which is the point $S_2$ rotated θ degrees with the point P as the center of rotation, is designated as $b_2$. Because the hues of the colored regions do not change in the radial direction extending outward from the center, a value $abs(a_1 - a_2)$ becomes smaller and a value $abs(a_1 - b_1)$ becomes greater, the closer the point P is to the center. Therefore, evaluation functions that evaluate whether the point P is the center of the color chart image are set.

First, an evaluation value Vr that evaluates whether the point P is the center of the color chart employing the R values from among the R, G, and B values is determined as follows.

$$Vr = \sum_{\theta=\theta_0}^{\theta_m} \{abs(a_{1r} \rightarrow b_{1r}) - abs(a_{1r} - b_{2r})\}$$

wherein $\theta_0 = 0°$, $\theta_1 = 30°$, $\theta_2 = 60°$ ... $\theta_m = 330°$ Similarly, evaluation functions Vg and Vb are obtained for the G values and the B values from among the R, G, and B values. Then, a total evaluation value V is determined as follows:

$$V = V_r + V_g + V_b$$

The point P is shifted in small increments, and the position at which the evaluation value V becomes maximal is determined as the central point.

Figure 9:
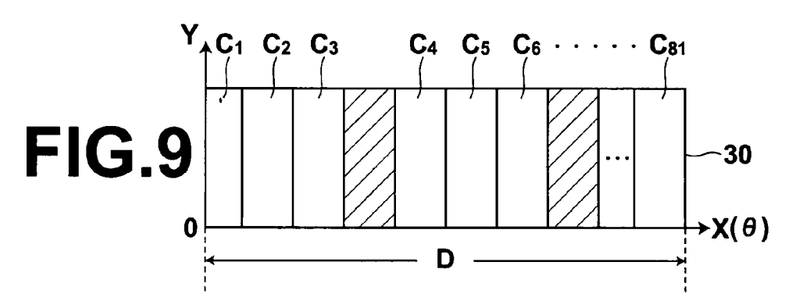
FIG. 9 is a diagram for explaining polar coordinate conversion of the radial color chart image into a rectangular color chart image.

Next, polar coordinate conversion is administered with the determined central point P as a reference, and the radial color chart image 20 is converted to the rectangular color chart 30 illustrated in FIG. 9. In FIG. 9, the X axis represents angular directions θ, and the Y axis represents distances from the point P. In the radial color chart 10, the RGB values are changed in a stepwise manner such that the color varies gradually in the circumferential direction. During polar coordinate conversion into the rectangular color chart image 30, adjacent colored regions at which the RGB values differ greatly are searched for, and designated as the first and last colored regions.

Figure 11A:
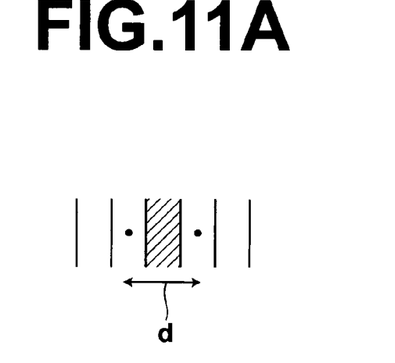
Figure 11B:
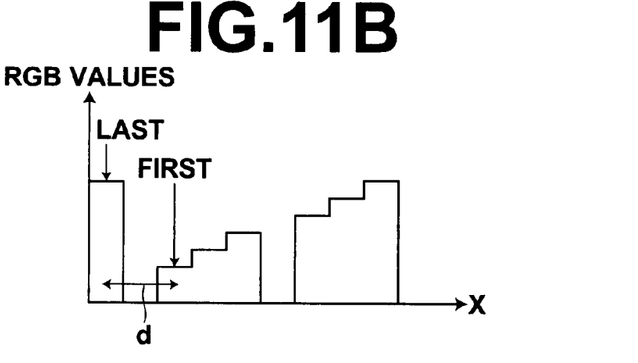

Here, the method by which the colored regions at which the RGB values differ greatly are searched for will be described. A single color chart 10 comprises 108 regions, of which 81 are colored regions and 27 are the neutral gray regions inserted for every three colored regions. When polar coordinate conversion is administered on the radial color chart image 20, a rectangular color chart image 30 comprising 108 regions is obtained, as illustrated in FIG. 9. Polar coordinate conversion is administered such that adjacent colored regions having a neutral gray region therebetween and having the greatest difference in the RGB values (the sum of the R, G, and B values) thereof are the first and last colored regions of the rectangular color chart image 30 (refer to FIG. 11B).

As illustrated in FIG. 9, in the case that the width of the rectangular color chart image 30 is D, the width of each of the colored regions will be D/108. The distance d between two colored regions having a neutral gray region therebetween is $d = (D/108) \times 2$ (refer to FIG. 11A). Therefore, positions which are d apart from each other and at which RGB values differ the most are searched for, to find the colored region which is to be the first region of the rectangular color chart image 30. The following evaluation value W is employed to determine the first colored region. Note that nine color charts 10 are prepared, and nine color chart images are obtained. However, because the R values are fixed in each of the color charts 10, the evaluation value W is determined based on the G and B values.

$$W = (G(x_i, y) - G(x_i + d, y) + B(x_i, y) - B(x_i + d, y))$$

wherein i is the ordinal number of the colored region

The colored regions at which the evaluation value W becomes maximal are designated as the first and last colored regions of the color chart image 30.

Figure 12A:
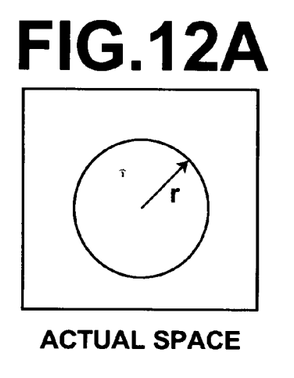
FIGS. 12A, 12B, and 12C are diagrams for explaining distortion in images obtained with a wide angel lens.
Figure 12B:
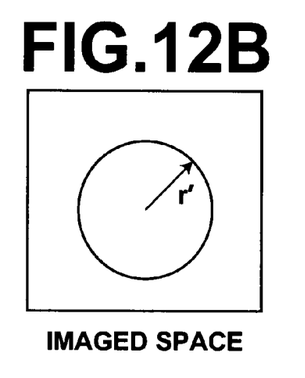
Figure 12C:
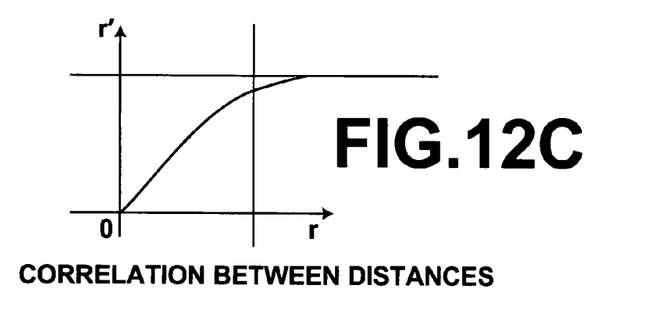

A wide angle lens is employed in the endoscope 100. Therefore, an actual distance r within the color chart 10 and a distance r' within the color chart image have the relationship indicated in FIG. 12. Therefore, the width of the colored regions will not be uniform in the case that the endoscope does not obtain an image centered on the center of the radial color chart 10.

In addition, because the endoscope 100 is designed to image the interiors of stomachs and intestines, the color red is easily imaged, whereas colors that do not exist within abdominal cavities, such as gray, cannot be reproduced. Therefore, the imaged neutral gray regions may appear reddish. Further, there are cases that the borders among the colored regions will appear dark and the centers of the colored regions will appear light, because edges such as those of the borders among the colored regions are emphasized during imaging.

The neutral gray regions are searched for within the obtained image, based on the grayness thereof. For example, the degree of grayness v is obtained by:

$$v = abs(R-G) + (R+G)$$

Figure 13A:
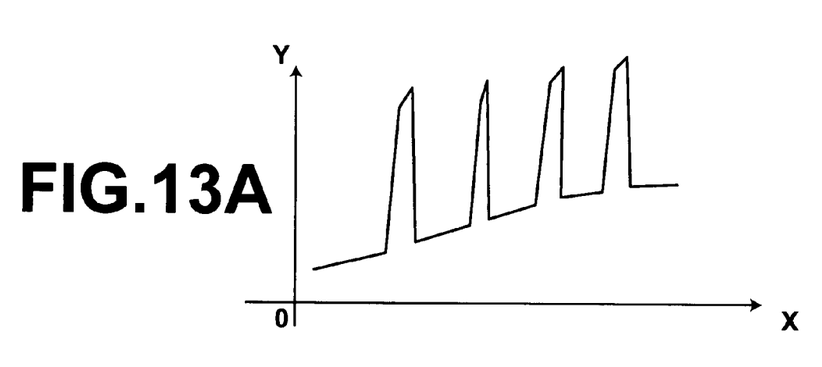

The degree of grayness v varies in the direction of the X axis within the rectangular color chart image 30 (refer to FIG. 9), as illustrated in FIG. 13A.

As illustrated in FIG. 13A, the probability is high that the locations where the degrees of grayness v are high are the neutral gray regions. However, there are endoscopes that tend to obtain images having yellowish tinges. In the case that endoscopes having the above characteristic obtain images of the color chart 10, gray areas appear to be blue, which is the complementary color of yellow, and the degrees of grayness v may assume peaks at regions other than the neutral gray regions. Therefore, whether the locations where the degrees of grayness v are high are actually the neutral gray regions is judged based on the intervals of the peaks and valleys within graphs that represent the degrees of grayness v. Corrected evaluation values v', in which the degrees of grayness v are emphasized at the intervals between the neutral gray regions such that degrees of grayness v are most emphasized at the actual neutral gray regions, are obtained according to the following formula, for example:

$$v' = v_x^2 + D/27$$

Figure 13B:
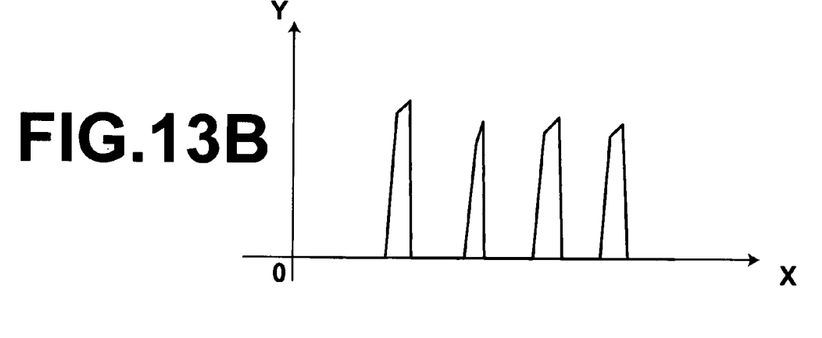

A morphology operation is administered on the evaluation values v', and the peaks in the degrees of grayness v' such as those illustrated in FIG. 13B are extracted to find the neutral gray regions.

Figure 14:
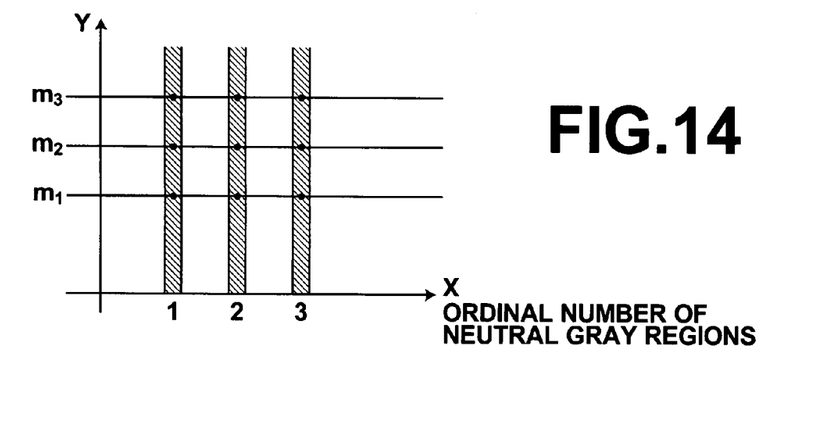
FIG. 14 is a graph for explaining how brightness is measured within neutral gray regions.

If the illuminating window 114 of the endoscope 100 is placed at the approximate center of the color chart 10, the RGB values of the neutral gray regions approach (255, 255, 255) at the central portion, and (0, 0, 0) at the peripheral portion. Therefore, a single neutral gray region (hatched portion) is selected from within the rectangular color chart image 30, and the RGB values therein are calculated. A position within the selected region at which the RGB values are close to (127, 127, 127) is searched for, and lines $m_1$, $m_2$, and $m_3$, which have uniform Y values within a coordinate system that represents the rectangular color chart image 30, are set in the vicinity thereof, as illustrated in FIG. 14 (that is, concentric circles having radii of predetermined distances from the central point P are set within the color chart image 20 prior to polar coordinate conversion). The lines are set such that the brightness $L_2$ along the line $m_2$ is $L_2=127$, the brightness $L_1$ along the line $m_1$ is $L_1>127$, and the brightness $L_3$ along the line $m_3$ is $L_3<127$.

Pixel values of points along the lines $m_1$, $m_2$, and $m_3$ (the black dots in FIG. 14) are extracted. The brightness L of each of the points is derived by the following equation:

$$L = (R+G+B)/3$$

(alternatively, $L = 0.3R + 0.6G + 0.1B$)

Figure 15A:
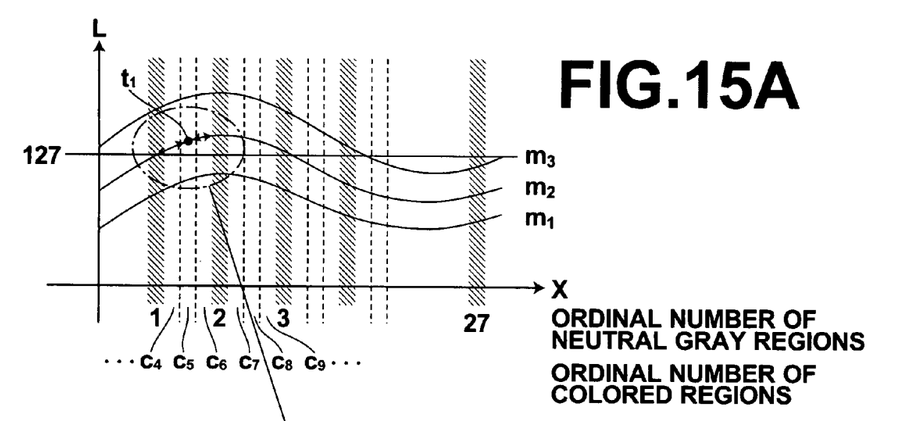
FIGS. 15A and 15B are diagrams for explaining how brightness within colored regions is estimated.
Figure 15B:
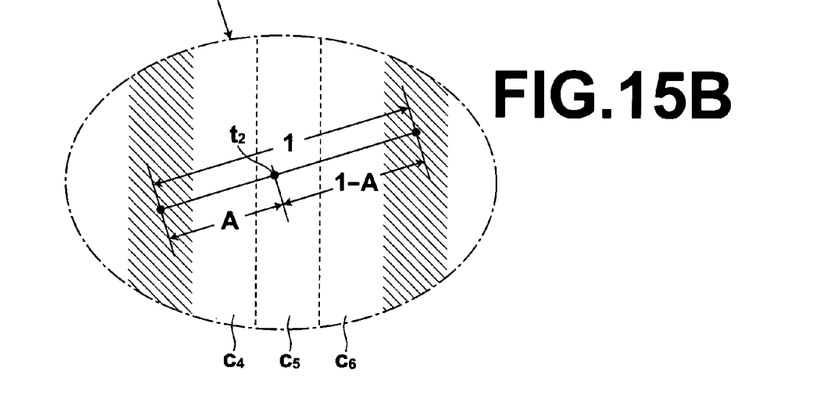
Figure 16:
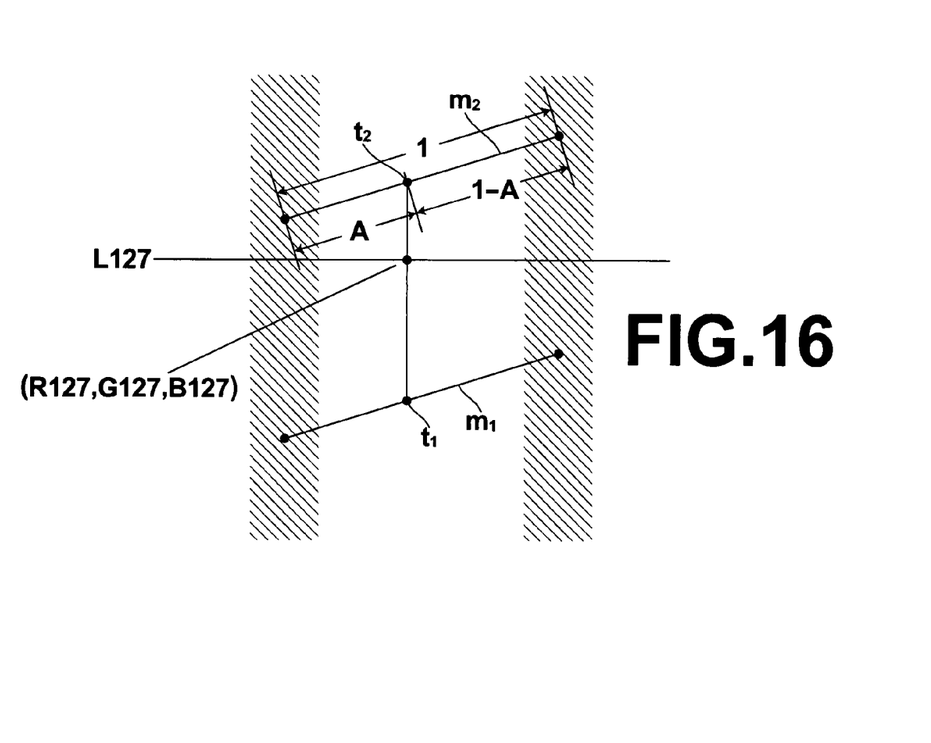
FIG. 16 is a diagram for explaining how RGB values of a position at which brightness is constant within a colored region are obtained.

When the brightness L of points along the lines $m_1$, $m_2$, and $m_3$ are interpolated into curves, the curves become those illustrated in the graph of FIG. 15A. The brightness L of each point within the neutral gray regions is known from the above equation. Therefore, the brightness L of the colored regions corresponding to the color of a subject is obtained by linear extrapolation, for example, employing the brightness of the neutral gray regions to either side of the colored regions. As illustrated in the magnified view of FIG. 15B, if the distance between the point in a neutral gray zone to the left of the colored regions and the point in a neutral gray zone to the right of the colored regions is designated as 1, the distance from the left neutral gray region to a sample point $t_2$ within the colored regions is designated as A, and the distance from the sample point $t_2$ to the right neutral gray region is designated as 1-A, the brightness L1[Color(i)] of the sample point $t_2$ can be obtained by the following equation:

$$L1[Color(i)] = L1[Left\_Gray(Color(i))] \times A + L1[Left\_Gray(Color(i))] \times (1-A)$$

wherein:

i is the ordinal number of the colored region;

L1[Left_Gray (Color(i))] is the brightness of the point along line $m_2$ within the left neutral gray region; and L1[Right_Gray (Color (i))] is the brightness of the point along line $m_2$ within the right neutral gray region;

Further, the RGB values at positions where L=127 within each of the colored regions are obtained. Two interpolated lines, of which the brightness straddles 127, are selected (for example, lines $m_1$ and $m_2$ in FIG. 16). The color of sample point $t_1$, of which the brightness is L1, is designated as (R1, G1, B1), the color of sample point $t_2$, of which the brightness is L2, is designated as (R2, G2, B2), and the R value $R_{127}$ of a point having a brightness of L=127 is determined by the following equation:

$$R_{127} = (R1(127-L2) + R2(L1-127))/(L1-L2)$$

The G value and the B value of the point having a brightness of L=127 can be obtained in a similar manner.

A three dimensional lookup table 3D-LUT1 is generated, with the RGB values ($R_{127}$, $G_{127}$, $B_{127}$) as a reference value for images obtained by the endoscope. Data of the color charts 10 are a combination of RGB values in the aforementioned nine steps of 0, 32, 64, 96, 127 . . . 255, and comprise $9^3=729$ colors. The values of the color charts 10 are correlated with the RGB values ($R_{127}$, $G_{127}$, $B_{127}$) at which the brightness is 127 for each colored region to generate the three dimensional lookup table 3D-LUT1. Specifically, for example, in the case that the RGB values within a colored region of the color chart 10 are (32, 32, 64) and the RGB values of the colored region within the color chart image 20 at which the brightness is 127 is (36, 30, 59), the RGB values (32, 32, 64) of the color chart 10 are correlated with the RGB values (36, 30, 59) of the color chart image. The three dimensional lookup table is generated for all of the colored regions in a similar manner.

Figure 17:
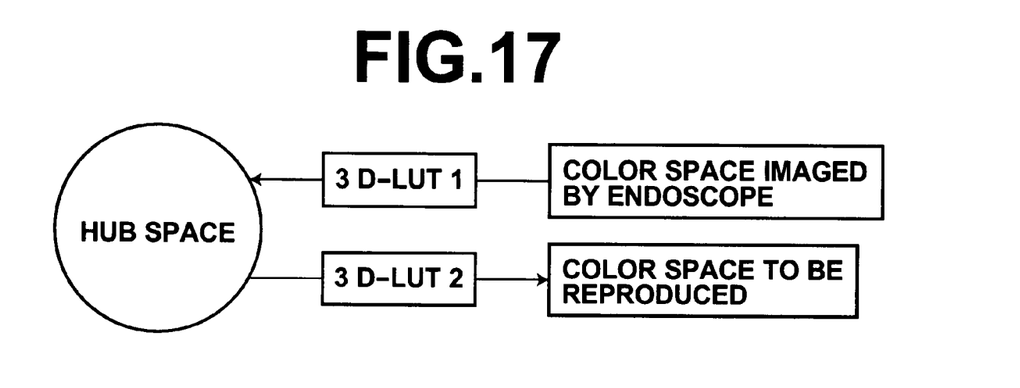
FIG. 17 is a diagram for explaining method of color adjustment.

The images obtained by the endoscope 100 are converted into a standard color space (hub space) employing the three dimensional lookup table 3D-LUT1, as illustrated in FIG. 17. Further, another three dimensional lookup table 3D-LUT2 for converting colors from the hub space to another color space may be generated, to reproduce images within the other color space, which takes diagnosis and color spaces unique to endoscopes into consideration. In this case, color conversion may be performed using the three dimensional lookup table 3D-LUT2, to reproduce images in colors suited for diagnosis.

As has been described in detail above, data obtained by endoscopes having various characteristics can be accurately converted into a desired color space for reproduction.

What is claimed is:

1. A method for adjusting colors within an image obtained by an endoscope, comprising the steps of:
   obtaining a color chart image of the color chart with the endoscope, from directly in front of the predetermined point of the color chart, said color chart comprising:
   a plurality of colored regions each being of a different color and separated by line segments that radiate outward from a predetermined point; and
   a plurality of achromatic colored regions which are provided among the plurality of colored regions at predetermined intervals;
   detecting the achromatic regions of the color chart from within the color chart image;
   estimating the brightness of the colored regions within the color chart image, based on the brightness of the achromatic regions; and
   adjusting the colors that appear within the image obtained by the endoscope, based on the pixel values at positions within the color chart image, at which the estimated brightness of the colored regions is constant.

2. A method for adjusting colors within an image obtained by an endoscope as defined in claim 1, wherein:
   adjustment of colors is performed by employing a look up table, in which pixel values at the positions within the color chart image at which the estimated brightness of the colored regions is constant are correlated to pixels values of the corresponding colored regions within the color chart.

3. A method for adjusting colors within an image obtained by an endoscope, comprising the steps of:
   obtaining a color chart image of the color chart with the endoscope, from directly in front of the predetermined point of the color chart, said color chart comprising:
   a plurality of colored regions each being of a different color and separated by line segments that radiate outward from a predetermined point; and
   a plurality of achromatic colored regions which are provided among the plurality of colored regions at predetermined intervals, wherein the achromatic colored regions are neutral gray regions;
   detecting the achromatic regions of the color chart from within the color chart image;
   estimating the brightness of the colored regions within the color chart image, based on the brightness of the achromatic regions; and
   adjusting the colors that appear within the image obtained by the endoscope, based on the pixel values at positions within the color chart image, at which the estimated brightness of the colored regions is constant.

4. A method for adjusting colors within an image obtained by an endoscope as defined in claim 3, wherein:
   adjustment of colors is performed by employing a look up table, in which pixel values at the positions within the color chart image at which the estimated brightness of the colored regions is constant are correlated to pixels values of the corresponding colored regions within the color chart.

5. A method for adjusting colors within an image obtained by an endoscope, comprising the steps of:
   obtaining a color chart image of the color chart with the endoscope, from directly in front of the predetermined point of the color chart, said color chart comprising:
   a plurality of colored regions each being of a different color and separated by line segments that radiate outward from a predetermined point; and
   a plurality of achromatic colored regions which are provided among the plurality of colored regions at predetermined intervals wherein the color chart is employed to adjust colors within images obtained by endoscopes;
   detecting the achromatic regions of the color chart from within the color chart image;
   estimating the brightness of the colored regions within the color chart image, based on the brightness of the achromatic regions; and
   adjusting the colors that appear within the image obtained by the endoscope, based on the pixel values at positions within the color chart image, at which the estimated brightness of the colored regions is constant.

6. A method for adjusting colors within an image obtained by an endoscope as defined in claim 5, wherein:
   adjustment of colors is performed by employing a look up table, in which pixel values at the positions within the color chart image at which the estimated brightness of the colored regions is constant are correlated to pixels values of the corresponding colored regions within the color chart.

7. A method for adjusting colors within an image obtained by an endoscope, comprising the steps of:
   obtaining a color chart image of the color chart with the endoscope, from directly in front of the predetermined point of the color chart, said color chart comprising:
   a plurality of colored regions each being of a different color and separated by line segments that radiate outward from a predetermined point; and
   a plurality of achromatic colored regions which are provided among the plurality of colored regions at predetermined intervals, wherein:
   the achromatic colored regions are neutral gray regions, wherein the color chart is employed to adjust colors within images obtained by endoscopes;
   detecting the achromatic regions of the color chart from within the color chart image;
   estimating the brightness of the colored regions within the color chart image, based on the brightness of the achromatic regions; and
   adjusting the colors that appear within the image obtained by the endoscope, based on the pixel values at positions within the color chart image, at which the estimated brightness of the colored regions is constant.

8. A method for adjusting colors within an image obtained by an endoscope as defined in claim 7, wherein:
   adjustment of colors is performed by employing a look up table, in which pixel values at the positions within the color chart image at which the estimated brightness of the colored regions is constant are correlated to pixels values of the corresponding colored regions within the color chart.

* * * * *